US008703762B2

(12) United States Patent
Albuquerque et al.

(10) Patent No.: US 8,703,762 B2
(45) Date of Patent: Apr. 22, 2014

(54) METHOD OF TREATING ORGANOPHOSPHOROUS POISONING

(75) Inventors: Edson X. Albuquerque, Baltimore, MD (US); Michael Adler, Bel Air, MD (US); Edna F.R. Pereira, Baltimore, MD (US)

(73) Assignees: University of Maryland Baltimore, Baltimore, MD (US); The United States of America as repr. by the Sec. of the Army, U.S. Army Med. Resr. Inst. of Chem. Defense, Washington, DC (US)

( * ) Notice: Subject to any disclaimer, the term of this patent is extended or adjusted under 35 U.S.C. 154(b) by 0 days.

(21) Appl. No.: 13/027,129

(22) Filed: Feb. 14, 2011

(65) Prior Publication Data
US 2011/0144093 A1 Jun. 16, 2011

Related U.S. Application Data

(63) Continuation of application No. 11/575,945, filed as application No. PCT/US2005/033789 on Sep. 23, 2005, now Pat. No. 7,888,346.

(60) Provisional application No. 60/613,121, filed on Sep. 24, 2004.

(51) Int. Cl.
*A01N 43/00* (2006.01)
*A01N 43/46* (2006.01)
*A61K 31/55* (2006.01)
*A01N 43/08* (2006.01)
*A61K 31/34* (2006.01)

(52) U.S. Cl.
USPC .......................................... 514/215; 514/468

(58) Field of Classification Search
None
See application file for complete search history.

(56) References Cited

U.S. PATENT DOCUMENTS

| 4,292,308 | A | * | 9/1981 | Sanders et al. ............... 424/542 |
|---|---|---|---|---|
| 4,550,113 | A | | 10/1985 | Lavretskaya et al. |
| 4,735,953 | A | | 4/1988 | Lavretskaya et al. |
| 5,480,651 | A | | 1/1996 | Callaway |
| 5,795,909 | A | | 8/1998 | Shashoua et al. |
| 5,939,095 | A | * | 8/1999 | Hille et al. ................... 424/449 |
| 6,099,863 | A | | 8/2000 | Gilis et al. |
| 6,114,347 | A | | 9/2000 | Hille et al. |
| 6,211,230 | B1 | | 4/2001 | Filbert et al. |
| 6,261,537 | B1 | | 7/2001 | Klaveness et al. |
| 6,264,917 | B1 | | 7/2001 | Klaveness et al. |
| 6,331,289 | B1 | | 12/2001 | Klaveness et al. |
| 6,358,941 | B1 | | 3/2002 | Snorrason et al. |
| 6,458,812 | B1 | | 10/2002 | McKittrick et al. |
| 6,576,636 | B2 | | 6/2003 | Webb et al. |
| 6,589,504 | B1 | | 7/2003 | Raub et al. |
| 6,602,902 | B2 | | 8/2003 | Shashoua et al. |
| 6,610,713 | B2 | | 8/2003 | Tracey |
| 6,617,361 | B2 | | 9/2003 | Eig |
| 6,670,356 | B2 | | 12/2003 | Davis |
| 6,680,047 | B2 | | 1/2004 | Klaveness et al. |
| 6,692,767 | B2 | | 2/2004 | Burnside et al. |
| 6,716,857 | B2 | | 4/2004 | Kim et al. |
| 6,720,427 | B2 | | 4/2004 | Sanner et al. |
| 6,756,385 | B2 | | 6/2004 | Sanner et al. |
| 6,759,419 | B2 | | 7/2004 | Kim et al. |
| 6,777,435 | B1 | | 8/2004 | Momose et al. |
| 6,838,471 | B2 | | 1/2005 | Tracey |
| 6,858,648 | B2 | | 2/2005 | Pan et al. |
| 6,900,202 | B2 | | 5/2005 | Imoto et al. |
| 6,906,081 | B2 | | 6/2005 | Hey et al. |
| 6,919,330 | B2 | | 7/2005 | Vaddadi et al. |
| 6,964,957 | B2 | | 11/2005 | Abreo et al. |
| 6,977,070 | B2 | | 12/2005 | Dugger, III |
| 7,001,908 | B2 | | 2/2006 | Godfrey et al. |
| 7,015,345 | B2 | | 3/2006 | Kawanishi et al. |
| 7,022,725 | B2 | | 4/2006 | Momose et al. |
| 7,030,081 | B2 | | 4/2006 | Nistri et al. |
| 7,034,019 | B2 | | 4/2006 | Kukla et al. |
| 7,034,039 | B2 | | 4/2006 | Oi et al. |
| 7,038,085 | B2 | | 5/2006 | Rariy et al. |
| 7,045,527 | B2 | | 5/2006 | Chen et al. |
| 7,060,270 | B2 | | 6/2006 | Nicolau et al. |
| 7,078,529 | B2 | | 7/2006 | Sanner et al. |
| 2005/0013869 | A1 | | 1/2005 | Chaw et al. |
| 2006/0172993 | A1 | | 8/2006 | Parys et al. |

FOREIGN PATENT DOCUMENTS

JP H09-506360 6/1997
WO 03/092606 A2 11/2003

OTHER PUBLICATIONS

Japanese Office Action issued on Oct. 12, 2011 in Japanese Patent Application No. 533601/2007, corresponding to the US Parent Patent No. 7,888,346-English Translation.
Dawson et al., "Some adjuncts to oxime-atropine therapy for organophosphate intoxication—Their effects on acetylcholinesterase," Biochem. Pharm., 28: 2211-2214 (1979).
Leaning et al., "Bloody Sunday," Report of a Medical Mission to Soviet Georgia, 1990, Physicians for Human Rights, pp. 1-82.
Samochocki et al., "Galantamine is an Allosterically Potentiating Ligand of Neuronal Nicotinic but Not of Muscarinic Acetylocholine Receptors," JPET, vol. 305: pp. 1024-1036 (2003).
Santos et al., "Low Concentrations of Pyridostigmine Prevent Soman-Induced Inhibition of GABAergic Transmission in the Central Nervous System: Involvement of Muscarinic Receptors," JPET, vol. 304: pp. 254-265 (2003).
Santos et al., "Spine Density and Dendritic Branching Pattern of Hippocampal CA1 Pyramidal Neurons in Neonatal Rats Chronically Exposed to the Organophosphate Paraoxon," NeuroToxicology, vol. 25: pp. 481-494 (2004).

(Continued)

*Primary Examiner* — James D Anderson
*Assistant Examiner* — Stephanie Springer
(74) *Attorney, Agent, or Firm* — Pedigo Law Firm, PLLC

(57) ABSTRACT

A method for treating organophosphorous poisoning (OP) comprising administering to a mammal at risk for OP poisoning an OP poisoning-inhibiting amount of galantamine.

17 Claims, No Drawings

(56) References Cited

OTHER PUBLICATIONS

Santos et al., "The Nicotinic Allosteric Potentiating Ligand Galantamine Facilitates Synaptic Transmission in the Mammalian Central Nervous System," Mol. Pharmacal., vol. 61: pp. 1222-1234 (2002).

Shabunova et al., "Effect of cholinesterase inhibitors on the electrical excitability of the membrane of frog muscle fiber," Fiziol Zh SSSR Im I M Sechenova, vol. 68:9 pp. 1223-1228 (1982) (Abstract).

International Search Report and Written Opinion dated Dec. 28, 2006 for International PCT Application No. PCT/US05/33789, National Stage entry of parent U.S. Appl. No. 11/575,945.

European Office Action dated Apr. 21, 2011 for European Patent Application No. 05 812 994.1, corresponding to parent Appl. No. 11/575,945.

Kugusheva, L. I. et al., Interaction of Membrane-Bound and Solubilized Acetylcholinesterase of Human 4 and Bovine Erythrocytes with Organophosphorus Inhibitors, journal, 1986, vol. 58 No. 3, pp. 13-18, Ukrainskii Biokhimicheskii Zhurnal, Russia.

Muggleton et al., Assessment of a Combination of Physostigmine and Scopolamine as Pretreatment Against the Behavioural Effects of Organophosphates in the Common Marmoset, journal, 2003, vol. 166 No. 3, pp. 212-220, Psychopharmacology, Springer-Verlag, Germany.

Storch et al., Physostigmine, galanthamine and codeine act as 'non-competitive nicotinic receptor agonists', on clonal rat pheochromoctyoma cells, journal, 1995, vol. 290 No. 3, pp. 207-219, European Journal of Pharmacology, Elsevier Science B.V., Netherlands.

Tonkopii et al., Study of Characteristics of the Interaction of Galanthamine with AcetylCholinEsterase of the Mouse Brain in In-Vivo Experiments, 1976, vol. 82 No. 7, pp. 823-825.

Tonkopii V. D., Oxidative stress in the mechanism of organophosphates neurotoxicity, 2003, vol. 144 No. Suppl. 1, pp. 132.

Australian Office Action for AU Application No. 2005289808, May 27, 2010, corresponding to parent U.S. Appl. No. 11/575,945.

Israeli Office Action for Application No. 182048, Jun. 23, 2011, corresponding to US parent U.S. Appl. No. 11/575,945.

Kenneth J. Keller, Overcoming Inhibitions, PNAS Sep. 5, 2006; vol. 103 No. 36; pp. 13263-13264.

Albuquerque et al., Effective countermeasure against poisoning by organophosphorous insecticides and nerve agents, PNAS Aug. 29, 2006; vol. 103 No. 35; pp. 13220-13225.

Bajgar JIR1: Organophosphates/nerve agent poisoning: mechanism of action, diagnosis, prophylaxis, and treatment', Advances in Clinical Chemistry, Academic Press, London, GB, vol. 38. Jan. 1, 2004, pp. 151-216, XPOO91 09278, ISSN: 0065-2423. DOI: 10.1016/S0065-2423 (04)38006-6.

Lopes et al.: "Competitive Antagonism between the Nicotinic Allosteric Potentiating Ligand Galantamine and Kynurenic Acid at $\alpha 7^*$ Nicotinic Receptors", Journal of Pharmacology and Experimental Therapeutist, Published online before print Apr. 19, 2007, doi: 10..1124/jpet.107.123109 JPET Jul. 2007 vol. 322 No. 1 48-58.

Ludwig et al.: "Localization by site-directed mutagenesis of a galantamine binding site on a7 nicotinic acetylcholine receptor extracellular domain ", Journal of Receptors and Signal Transduction, 2010; 30(6): 469-483.

Mamczarz et al."Galantamine counteracts development of learning impairment in guinea pigs exposed to the organophosphorus poison soman: Clinical significance", NeuroToxicology 32 (2011), pp. 785-798.

Pereira et al., "Unconventional Ligands and Modulators of Nicotinic Receptors", Wiley Periodicals Inc. 2002, pp. 479-500.

Samochocki et al: "Galantamine is an allosterically potentiating ligand of the human $\alpha 4/\beta 2$ nAChR", ACTA Neurologica Scandinavica 2000: Supplement 176: pp. 68-73.

Bajgar: J.Med. Chem. Def., Feb. 2004, vol. 1, pp. 1-16.

\* cited by examiner

METHOD OF TREATING ORGANOPHOSPHOROUS POISONING

This application claims the benefit of U.S. Provisional Patent Application No. 60/613,121, filed Sep. 24, 2004.

STATEMENT OF GOVERNMENT SUPPORT

The invention described herein was made, at least in part, with funding from the U.S. Army under Grant No. DAAD19-02-D-0001. Therefore, the United States of America may have certain rights in the invention.

TECHNICAL FIELD OF THE INVENTION

The present invention relates to a method of treating organophosphorous poisoning in an animal, in particular a mammal, specifically a human.

BACKGROUND OF THE INVENTION

Organophosphorous compounds (OPs), due to their physical state and high lipophilicity, rapidly penetrate and accumulate in the central nervous system (CNS). OP poisoning of military personnel on the battlefield and of common citizens in the event of a terrorist attack with nerve gas, for example, has caused an increase in concern for public and governmental authorities around the world in recent years. In addition, increased demands for food and ornamental crops have resulted in an increase in the use of toxic anti-cholinesterase (anti-ChE)-based pesticides, including OPs such as parathion and malathion, in developed and developing countries. This has resulted in an increase in the accidental poisoning of farmers and gardeners.

It has long been known that the main toxic effects of OPs and other anti-ChE agents result from the inhibition of the enzyme ChE, which is responsible for the inactivation of the neurotransmitter acetylcholine (ACh) in the CNS and peripheral nervous system (PNS), thereby abnormally increasing and prolonging muscarinic and nicotinic cholinergic responses. Unfortunately, current methods to treat or prevent the toxic effects of OPs are still far from acceptable, particularly in the event of acute exposure to nerve agents that are highly absorbable and readily accessible to the brain.

Reversible ChE inhibitors, such as pyridostigmine bromine (PB), physostigmine, and huperzine, have been tested as antidotal therapy against OP poisoning. PB has been used as a preventive treatment by soldiers in the field. While it is a powerful anti-ChE agent, its action is mostly limited to the PNS, due to the fact that it is a charged molecule that hardly penetrates the CNS. Therefore, PB does not effectively confer protection of brain ChE against nerve gases. Physostigmine is more effective than PB, but less safe. Therefore, there currently is no method of protecting the brain from irreversible ChE inhibition by OPs. Rather, those individuals, who have been exposed to OP, have been treated post-exposure with antimuscarinic agents, such as atropine, ChE reactivators, such as oximes, e.g., pyridine-2-aldoxime (2-PAM), and anti-convulsants, e.g., Diazepam.

In view of the above, it is an object of the present invention to provide a method of treating OP poisoning. This and other objects and advantages, as well as additional inventive features, will become apparent from the detailed description provided herein.

BRIEF SUMMARY OF THE INVENTION

The present invention provides a method of treating OP poisoning. The method comprises administering to a mammal at risk for OP poisoning an OP poisoning-inhibiting amount of galantamine, whereupon the mammal is protected from OP poisoning upon exposure to an OP.

DETAILED DESCRIPTION OF THE INVENTION

The present invention is predicated, at least in part, on the surprising and unexpected discovery, that a tertiary alkaloid, such as galantamine, can be administered to an animal, in particular a mammal, specifically a human, at risk of OP poisoning to protect the animal from OP poisoning. While galantamine is a weaker ChE inhibitor as compared to PB and physostigmine, it is a non-charged molecule and, therefore, has the ability to pass through the blood-brain barrier. Galantamine also functions as an allosteric potentiating ligand (APL) of nicotinic receptors (nAChRs), and is able to "rescue" some nicotinic receptors from desensitization. This property is important in the context of OP poisoning when excess ACh induces massive desensitization of nAChRs.

In view of the above, the present invention provides a method for antidotal therapy of OP poisoning. The method comprises administering to a mammal at risk for OP poisoning an OP poisoning-inhibiting amount of galantamine, whereupon the mammal is protected from OP poisoning upon subsequent exposure to an OP. The galantamine can be administered to the mammal before or after exposure to an OP. If galantamine is administered before exposure, the method further comprises subsequently administering to the mammal an effective amount of an antimuscarinic agent, such as atropine. If galantamine is administered after exposure, the method further comprises administering an effective amount of an antimuscarinic agent, such as atropine, after exposure to an OP and prior to or simultaneously with an OP-poisoning inhibiting effective amount of galantamine. Preferably, the antimuscarinic agent and galantamine are administered as soon as possible after exposure to an OP in order to maximize the effectiveness of the post-treatment. Depending on the timing of subsequent administration of the antimuscarinic agent and galantamine in relation to the time of exposure to an OP, this embodiment can have therapeutic effects as well.

A mammal is at risk for OP poisoning if it is currently exposed to or is at risk of being exposed to a level of OP that is sufficiently high to poison the mammal. Such risk exists for military personnel on the battlefield, common citizens in the event of a terrorist attack with nerve gas, and farmers and gardeners who work with food and ornamental crops treated with anti-ChE-based pesticides.

An amount of galantamine is an "OP poisoning-inhibiting amount" or an "effective amount" when it is sufficient to diminish significantly, preferably completely, the detrimental effects of exposure to OPs as evidenced by signs of ill health, including but not limited to, any peripheral and central hypercholinergic signs of OP intoxication, such as hypersecretion, muscle contraction, respiratory difficulties, convulsion, or behavioral abnormalities. Amounts of galantamine that are sufficient to inhibit OP poisoning can be determined in accordance with dosage range-finding techniques as are known in the art. For example, an optimal dose can be determined by a skilled clinician in a clinical setting or in the field. Generally, optimal doses are determined by incrementally altering an initial dose until the optimum effect under the circumstances is achieved. Doses of galantamine, such as galantamine hydrobromide, ranging from about 5 mg/kg to about 8 mg/kg effectively prevent toxicity and lethality induced by lethal doses of the nerve agents soman and sarin when 10 mg/kg atropine, such as atropine sulfate, are also administered. Galantamine is an effective antidotal therapy when used acutely for up to about 1 hr before or up to about 5 min after exposure to an OP.

Galantamine is commercially available from Hande Industry & Trade Holdings Co., Ltd., Shenzhen, China, among others. Desirably, the galantamine is suitable for administration to an animal, such as a mammal, in particular a human, as a pharmaceutical composition. The formulation of pharmaceutical compositions is known in the art (see, e.g., *Remington: The Science and Practice of Pharmacy*, Mack Pub. Co.). Galantamine is currently available as a pharmaceutical composition under the name Reminyl™ (Janssen-Cilag, Ltd., UK) for the treatment of Alzheimer's disease.

The galantamine can be administered by any suitable route of administration as is known in the art. Preferred routes of administration include, but are not limited to, oral and intramuscular. The route of administration will depend, in part, upon the circumstances of risk of exposure. For example, oral administration can be preferred for pre-treatment of a predicted exposure, as in the case of farm workers and other individuals who handle OP insecticides on a regular basis, e.g., daily, whereas intramuscular administration can be preferred for post-treatment of military personnel on the battlefield and civilians exposed to OPs, such as in the context of a terrorist attack.

If the mammal is exposed to an OP after administration of galantamine, preferably, an effective amount of an antimuscarinic agent, such as atropine, is administered to the mammal as soon as possible after exposure to the OP. The antimuscarinic agent can be administered by any suitable route. Intramuscular administration is normally preferred. An amount of an antimuscarinic agent, such as atropine, is an "effective amount" when it is sufficient to inhibit, preferably prevent, any adverse effects of exposure to OP. An effective amount of an antimuscarinic agent can be determined in accordance with dosage range-finding techniques as are known in the art. For example, an optimal dose can be determined by a skilled clinician in a clinical setting or in the field. Generally, optimal doses are determined by incrementally altering an initial dose until the optimum effect under the circumstances is achieved. As mentioned above, about 10 mg/kg is the most effective dose of atropine, such as atropine sulfate, when galantamine, such as galantamine hydrobromide, is administered in a dose of about 5 mg/kg to about 8 mg/kg.

Atropine is available from Sigma Chemical Co. (St. Louis, Mo.). Desirably, the atropine or other antimuscarinic agent is suitable for administration to an animal, such as a mammal, in particular a human, as a pharmaceutical composition (see, e.g., Remington, supra).

EXAMPLES

The following examples serve to illustrate the present invention but are not intended to limit its scope in any way.

Example 1

This example demonstrates the effectiveness of pre-treatment with galantamine in a mammal subsequently exposed to an OP.

Galantamine (4-10 mg/kg) was administered (intramuscularly) to guinea pigs (young males weighing 300-420 g) 30 min prior to or 5 min after exposure of the guinea pigs to 1.5-2.0× the 50% lethal dose (LD50) of soman (42 or 56 μg/kg subcutaneous injection) or sarin (63 or 73.5 μg/kg subcutaneous injection). Atropine sulfate (6-16 mg/kg) was administered (intramuscularly) to some of the guinea pigs 1-2 min after administration of the nerve agent soman or sarin. Simultaneously with or subsequently to (e.g., within about 4 min) atropine administration, some of the guinea pigs received galantamine (intramuscularly). Control guinea pigs received galantamine (4-8 mg/kg), atropine (6-16 mg/kg), a combination thereof, or saline. Survival and body weight were followed for at least one week.

Galantamine was found to protect the guinea pigs against lethal doses of soman or satin. A treatment consisting of 5-8 mg/kg galantamine and 10 mg/kg atropine fully protected the guinea pigs against toxicity and lethality induced by 1.5× LD50s of soman and sarin. Not only did galantamine fully protect the guinea pigs against death but, shortly after OP injection, the guinea pigs did not show any peripheral and central hypercholinergic signs of OP intoxication, such as hypersecretion, muscle contraction, respiratory difficulties, convulsion, or behavioral abnormalities, and, during the observation period of up to 1-2 weeks, they showed no signs of ill health. Those guinea pigs that received soman or sarin followed by atropine sulfate all presented life-threatening symptoms within 10-20 min and were euthanized as per the IACUC-approved protocol for animal care and handling.

In the first 24 hr, all guinea pigs receiving OP showed 5-10% weight loss; however, in the following days, the guinea pigs gained weight. With galantamine doses giving partial protection, some guinea pigs showed signs of OP intoxication. These guinea pigs had life-threatening symptoms within hours or days after the OP challenge and were euthanized as per the IACUC-approved protocol for animal care and handling. Such guinea pigs showed different degrees of OP toxicity and did not recover their body weights. However, after 3-4 days following the OP challenge, no further deaths were recorded. Control guinea pigs receiving either galantamine (up to 8 mg/kg) or atropine (6-10 mg/kg) or the mixture of the two protecting agents showed no loss of body weight or other untoward effects or signs of intoxication.

When the guinea pigs were euthanized by decapitation following deep anesthesia with $CO_2$, blood samples (obtained by cardiac puncture) and whole brains were removed and immediately frozen in dry ice for subsequent analysis of cholinesterase inhibition and galantamine levels. Initial measurements indicated that intramuscular injection of 8 mg/kg galantamine resulted in plasma and brain concentrations of the agent of approximately 1-3 μM, which are similar to the concentrations of galantamine observed in the plasma of humans treated with doses of galantamine clinically recommended for treatment of Alzheimer's disease. The concentrations of galantamine in the brain are sufficient to prevent desensitization of nAChRs by rising levels of ACh resulting from OP-induced irreversible inhibition of cholinesterases. Cholinesterase inhibition in the brain was in the range of 20% to <1% from the highest to the lowest measured concentrations of galantamine. Even when brain cholinesterase inhibition was negligible, galantamine still arrested OP-induced toxicity.

The brains of those guinea pigs that were successfully protected from OP poisoning by pre- or post-treatment with galantamine were compared to those of control guinea pigs morphometrically using Fluoro Jade B staining. Neuronal viability and structures were very similar in the brains of control and (galantamine+atropine)-treated, OP-challenged animals.

Example 2

This example demonstrates the effectiveness of post-treatment with galantamine in a mammal, which has been exposed to an OP.

Soman (42 µg/kg) was administered (subcutaneously) to guinea pigs (young males weighing 300-420 g). After 1 min, atropine (10 mg/kg) was administered (intramuscularly) to the animals. Simultaneously with or subsequently to (e.g., 4 min later) atropine administration, galantamine (8-10 mg/kg) was administered (intramuscularly) to the animals. Administration of 8-10 mg/kg galantamine within 5 min of administration of soman provided 100% protection. In contrast, administration of 6 mg/kg galantamine within 5 min of administration of soman only provided approximately 35% survival. In the first 24 hrs, all guinea pigs showed about a 5% weight loss; however, in the following days, the guinea pigs gained weight at the same rate as control animals that were not challenged with OPs.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A method of protecting a mammal from organophosphorous (OP) poisoning, which method comprises administering to a mammal after exposure to an OP poison an OP poisoning-inhibiting amount of galantamine sufficient to diminish the detrimental effects of exposure to OP and in the absence of administration of antimuscarinic agent before exposure.

2. The method of claim 1 further comprising the step of administering to the mammal after an OP exposure that produces peripheral and central hypercholinergic signs of OP intoxication an effective amount of an antimuscarinic agent sufficient to inhibit adverse muscarinic effects of exposure to OP.

3. The method of claim 2, wherein the antimuscarinic agent is atropine.

4. The method of claim 1 wherein the detrimental effects of OP exposure include muscarinic or nicotinic cholinergic responses.

5. The method of claim 1 wherein the detrimental effects of OP exposure are selected from the group consisting of: hyper secretion, muscle contraction, respiratory difficulties, convulsion, and behavioral abnormalities, and combinations thereof.

6. The method of claim 1 wherein the detrimental effects of OP exposure comprises loss of neuronal viability and protecting a mammal from OP poisoning includes administering galantamine in an amount sufficient to preserve or restore neuronal structures.

7. The method of claim 1 wherein galantamine is galantamine hydrobromide.

8. The method of claim 1 wherein galantamine is administered in an OP poisoning-inhibiting amount determined in accordance with dosage range-finding techniques.

9. The method of claim 1 wherein galantamine is administered in a clinical setting or in the field in an OP-poisoning inhibiting amount, the amount determined by administering an initial dose and then incrementally altering the initial dose to achieve an optimum effect under the circumstances.

10. The method of claim 1 wherein galantamine is administered in an amount effective to arrest OP-induced toxicity, the effective amount determined as establishing galantamine-induced cholinesterase inhibition in the brain of from a negligible amount to about 20%.

11. The method of claim 10 wherein the amount of cholinesterase inhibition established in the brain ranges from less than 1% to about 20%.

12. The method of claim 1 wherein galantamine is administered orally or intramuscularly.

13. A method of protecting a mammal from loss of neuronal viability by exposure to organophosphorous (OP) poison, which method comprises administering to a mammal after exposure to an OP poison, and in the absence of administering antimuscarinic agent before exposure, an amount of galantamine sufficient to preserve neuronal structures.

14. The method of claim 13 wherein galantamine is administered in an amount sufficient to rescue nicotinic receptors from desensitization or to protect against desensitization.

15. The method of claim 13 wherein galantamine is administered in an amount sufficient to preserve neuronal structures, the amount determined by administering an initial dose and then incrementally altering the initial dose to achieve an optimum effect on behavioral abnormalities under the circumstances.

16. The method of claim 13 wherein galantamine is galantamine hydrobromide.

17. A method for rescuing nicotinic receptors from and restoring or preserving neuronal viability after OP exposure, the method comprising the step of administering to a mammal following OP exposure, and in the absence of administering antimuscarinic agent prior to exposure, an amount of galantamine hydrobromide sufficient to establish galantamine-induced cholinesterase inhibition in the brain of from a negligible amount to about 20%.

* * * * *

UNITED STATES PATENT AND TRADEMARK OFFICE
CERTIFICATE OF CORRECTION

PATENT NO. : 8,703,762 B2
APPLICATION NO. : 13/027129
DATED : April 22, 2014
INVENTOR(S) : Edson X. Albuquerque et al.

Page 1 of 1

It is certified that error appears in the above-identified patent and that said Letters Patent is hereby corrected as shown below:

In The Specification

Column 1, lines 4 and 5 just beneath the title:

This application claims the benefit of U.S. Provisional Patent Application No. 60/613,121, filed Sep. 24, 2004.

Should read

--This application is a continuation of U.S. Application No. 11/575,945, filed on March 23, 2007, and now issued as U.S. Patent No. 7,888,346, which was the National Stage of International Application No. PCT/US2005/033789, filed on September 23, 2005 and now expired, which claims the benefit of U.S. Provisional Application No. 60/613,121, filed September 24, 2004.--

Column 1, lines 8-12 below "Statement Of Government Support"

The invention described herein was made, at least in part, with funding from the U.S. Army under Grant No. DAAD19-02-D-0001. Therefore, the United States of America may have certain rights in the invention.

Should read

--This invention was made with government support under Grant Numbers NS025296 and ES007263 awarded by the national Institutes of Health and Grant Numbers DAAD19-02-D-0001 and DAMD17-95-C-5063 awarded by the US Army. The government has certain rights in the invention.--

Signed and Sealed this
Twentieth Day of January, 2015

Michelle K. Lee
*Deputy Director of the United States Patent and Trademark Office*

UNITED STATES PATENT AND TRADEMARK OFFICE
CERTIFICATE OF CORRECTION

PATENT NO. : 8,703,762 B2  
APPLICATION NO. : 13/027129  
DATED : April 22, 2014  
INVENTOR(S) : Edson X. Albuquerque et al.

Page 1 of 1

It is certified that error appears in the above-identified patent and that said Letters Patent is hereby corrected as shown below:

IN THE SPECIFICATION

Column 1, lines 8-12 below "STATEMENT OF GOVERNMENT SUPPORT":

This invention was made with government support under Grant Numbers NS025296 and ES007263 awarded by the national Institutes of Health and Grant Numbers DAAD19-02-D-0001 and DAMD17-95-C-5063 awarded by the US Army. The government has certain rights in the invention.

REPLACE WITH:

--This invention was made with government support under grant numbers NS025296 and ES007263 awarded by the National Institutes of Health and grant number DAMD17-95-C-5063 awarded by the ARMY/MRMC and grant number DAAD19-02-D-0001 awarded by the ARMY/ARO. The government has certain rights in the invention.--

Signed and Sealed this  
Twenty-second Day of December, 2015

Michelle K. Lee  
*Director of the United States Patent and Trademark Office*